US00PP18208P2

(12) United States Plant Patent
Stewart

(10) Patent No.: US PP18,208 P2
(45) Date of Patent: Nov. 13, 2007

(54) ***ANIGOZANTHOS* PLANT NAMED 'RAMBUDAN'**

(50) Latin Name: *Anigozanthos flavidus*
Varietal Denomination: Rambudan

(75) Inventor: Ian Angus Stewart, Somersby (AU)

(73) Assignee: Ramm Botanicals Holdings Pty. Ltd., Tuggerah, NSW (AU)

( * ) Notice: Subject to any disclaimer, the term of this patent is extended or adjusted under 35 U.S.C. 154(b) by 0 days.

(21) Appl. No.: 11/450,767

(22) Filed: Jun. 9, 2006

(51) Int. Cl.
*A01H 5/00* (2006.01)

(52) U.S. Cl. ..... Plt./362
(58) Field of Classification Search ..... Plt./362
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Anigozanthos* plant named 'Rambudan', characterized by its compact, upright and somewhat outwardly spreading plant habit; freely and early flowering habit; freely branched flowering stems; and large red and green bi-colored flowers.

1 Drawing Sheet

Botanical designation: *Anigozanthos flavidus.*
Cultivar denomination: 'Rambudan'.

BACKGROUND OF THE INVENTION

The present invention relates to a new and distinct cultivar of *Anigozanthos,* botanically known as *Anigozanthos flavidus,* commonly referred to as Kangaroo-Paw, and hereinafter referred to by the name 'Rambudan'.

The new *Anigozanthos* is a product of a planned breeding program conducted by the Inventor in Tuggerah, New South Wales, Australia. The objective of the breeding program is to create new compact *Anigozanthos* cultivars that are suitable for container production, are freely flowering and have bright flower coloration.

The new *Anigozanthos* originated from a cross-pollination made by the Inventor on Nov. 9, 1998 in Tuggerah, New South Wales, Australia of a proprietary selection of *Anigozanthos flavidus* identified as code number H0061, not patented, as the female, or seed, parent with the *Anigozanthos flavidus* cultivar Emerald Gem, not patented, as the male, or pollen, parent. The new *Anigozanthos* was discovered and selected by the Inventor as a single flowering plant within the progeny of the stated cross-pollination in a controlled environment in Tuggerah, New South Wales, Australia.

Asexual reproduction of the new *Anigozanthos* by in vitro propagation of micro-plants in Tuggerah, New South Wales, Australia since September, 2000, has shown that the unique features of this new *Anigozanthos* are stable and reproduced true to type in successive generations.

SUMMARY OF THE INVENTION

The cultivar Rambudan has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Rambudan'. These characteristics in combination distinguish 'Rambudan' as a new and distinct cultivar of *Anigozanthos:*

1. Compact, upright and somewhat outwardly spreading plant habit.
2. Freely and early flowering habit.
3. Freely branched flowering stems.
4. Large red and green bi-colored flowers.

Plants of the cultivar Rambudan can be compared to plants of the female parent selection. In side-by-side comparisons conducted in Tuggerah, New South Wales, Australia, plants of the new *Anigozanthos* and the female parent selection differed in the following characteristics:

1. Plants of the new *Anigozanthos* had longer leaves than plants of the female parent selection.
2. Plants of the new *Anigozanthos* had longer flowers than plants of the female parent selection.
3. Plants of the new *Anigozanthos* had longer flowering stems than plants of the female parent selection.

Plants of the cultivar Rambudan can be compared to plants of the male parent, the cultivar Emerald Gem. In side-by-side comparisons conducted by the Inventor in Tuggerah, New South Wales, Australia, plants of the new *Anigozanthos* and the cultivar Emerald Gem differed in the following characteristics:

1. Plants of the new *Anigozanthos* had shorter leaves than plants of the cultivar Emerald Gem.
2. Plants of the new *Anigozanthos* had green and red-colored flowers whereas plants of the cultivar Emerald Gem had green-colored flowers.
3. Plants of the new *Anigozanthus* had shorter flowers than plants of the cultivar Emerald Gem.

Plants of the new *Anigozanthos* can be compared to plants of the cultivar Royal Cheer, not patented. In side-by-side comparisons conducted in Tuggerah, New South Wales, Australia, plants of the new *Anigozanthos* differed from plants of the cultivar Royal Cheer in the following characteristics:

1. Plants of the new *Anigozanthos* had shorter inflorescences than plants of the cultivar Royal Cheer.

2. Flowers of plants of the new *Anigozanthos* had a larger proportion of red coloration than flowers of plants of the cultivar Royal Cheer.
3. Peduncles of plants of the new *Anigozanthos* were more pubescent than peduncles of plants of the cultivar Royal Cheer.

Plants of the cultivar Rambudan can also be compared to plants of the cultivar Bush Emerald, disclosed in U.S. Plant Pat. No. 6,486. In side-by-side comparisons conducted by the Inventor in Tuggerah, New South Wales, Australia, plants of the new *Anigozanthos* and the cultivar Bush Emerald differed in the following characteristics:

1. Plants of the new *Anigozanthos* had shorter inflorescences than plants of the cultivar Bush Emerald.
2. Flowers of plants of the new *Anigozanthos* had a larger proportion of red coloration than flowers of plants of the cultivar Bush Emerald.

BRIEF DESCRIPTION OF THE PHOTOGRAPHS

The accompanying colored photographs illustrate the overall appearance of the new *Anigozanthos,* showing the colors as true as it is reasonably possible to obtain in colored reproductions of this type. Colors in the photographs may differ slightly from the color values cited in the detailed botanical description which accurately describe the colors of the new *Anigozanthos.*

The photograph at the bottom of the sheet comprises a side perspective view of a typical flowering plant of 'Rambudan' grown in a container.

The photograph at the top of the sheet comprises a close-up of a typical flowering stem of 'Rambudan'.

DETAILED BOTANICAL DESCRIPTION

The photographs and following observations, measurements and values describe plants grown in Lompoc, Calif., under commercial practice during the winter and early spring in a polycarbonate-covered greenhouse with day temperatures ranging from 18° C. to 24° C., night temperatures ranging from 16° C. to 18° C., and light levels ranging from about 4,000 to 8,000 foot candles. Plants were grown for about 27 weeks with one plant per 12.5-cm container. In the following description, color references are made to The Royal Horticultural Society Colour Chart, 1995 Edition, except where general terms of ordinary dictionary significance are used.

Botanical classification: *Anigozanthos flavidus* cultivar Rambudan.

Parentage:

*Female, or seed, parent.*—Proprietary selection of *Anigozanthos flavidus* identified as code number H0061, not patented.

*Male, or pollen, parent.*—*Anigozanthos flavidus* cultivar Emerald Gem, not patented.

Propagation:

*Type.*—In vitro propagation of micro-plants.

*Time to initiate roots, summer.*—About one week at temperatures of 25° C.

*Time to initiate roots, winter.*—About two weeks at temperatures of 15° C.

*Time to produce a rooted young plant, summer.*—About 45 to 60 days at temperatures of 25° C.

*Time to produce a rooted young plant, winter.*—About 55 to 70 days at temperatures of 15° C.

*Root description.*—Thick, fibrous; white in color.

*Rooting habit.*—Moderately branching.

Plant description:

*Plant and growth habit.*—Inverted triangle; compact, upright and somewhat outwardly spreading plant habit with branched flowering stems with red and green bi-colored flowers. Leaves in tight clumps. Moderately vigorous growth habit.

*Plant height* (*soil level to top of leaves*).—About 21 cm.

*Plant height* (*soil level to top of flowers*).—About 46 cm.

*Plant diameter.*—About 30 cm by 34 cm.

Lateral branch description:

*Number per plant.*—About 23.

*Length.*—About 2.2 cm.

*Diameter.*—About 4 mm.

*Internode length.*—About 3 mm.

*Strength.*—Strong.

*Texture.*—Smooth, glabrous.

*Color.*—145A.

Foliage description:

*Arrangement.*—Alternate equitant, simple; sessile.

*Length.*—About 22 cm.

*Width.*—About 1.6 cm.

*Shape.*—Ensiform; folded at base.

*Apex.*—Acute.

*Base.*—Clasping.

*Margin.*—Entire.

*Texture, upper and lower surfaces.*—Smooth, glabrous; towards the margins, pubescent; thick, leathery.

*Venation pattern.*—Parallel.

*Color.*—Developing foliage, upper and lower surfaces: 146D. Fully expanded foliage, upper surface: 146B; venation, 146B. Fully expanded foliage, lower surface: 147A; venation, 147A.

Flower description:

*Flower arrangement and habit.*—Large flowers arranged singly on terminal and axillary racemes. Flowers with tubular perianth; zygomorphic. Flowers held initially upright then curving outwards and eventually reflex with development. Flowers not fragrant. Freely flowering habit, about 18 to 34 flowers and flower buds develop per flowering stem.

*Natural flowering season.*—Plants flower throughout the summer in Southern California; flowering continuous during this period. Flowers last about 25 to 30 days on the plant. Flowers persistent.

*Inflorescence height.*—About 24 cm.

*Inflorescence diameter.*—About 9 cm.

*Flower diameter.*—About 1.5 cm.

*Flower height.*—About 4.7 cm.

*Flower buds.*—Length: About 5 cm. Diameter: About 7 mm. Shape: Tubular, curved. Texture: Tomentose. Color: Towards the base, 53B; towards the apex, 146A.

*Perianth.*—Arrangement: Fused elongated tube with six reflexed acute petal apices; split on lower surface. Perianth tube length: About 4.7 cm. Perianth tube diameter: About 1.3 cm; towards the base, about 8 mm. Petal apex length: About 9 mm. Petal apex width: About 3 mm. Texture, outer surface of perianth tube: Tomentose. Texture, inner surface of perianth tube; Smooth, glabrous. Color: When opening and fully opened, outer surface of perianth tube: Brighter than 146A; towards the base, 53B. When opening and fully opened, inner surface of perianth tube: 144A.

*Floral bracts.*—Length: About 1.5 cm. Width: About 4 mm. Shape: Ensiform. Apex: Acuminate. Base: Clasping. Margin: Entire. Texture, upper surface: Smooth, glabrous. Texture, lower surface: Tomentose. Color, upper surface: 146A. Color, lower surface: 53B.

*Peduncles* (*flowering stems*).—Length: About 33 cm. Diameter: About 5 mm. Angle: Upright to somewhat outwardly spreading. Strength: Strong, stout. Texture: Tomentose. Color: 53A.

*Pedicels* (*individual flower stems*).—Length: About 1.3 cm. Diameter: About 3 mm. Angle: Initially appressed to flowering stems, with development, about 30° to 45° from flowering stems. Strength: Strong. Texture: Tomentose. Color: 53A.

*Reproductive organs.*—Stamens: Quantity: Six per flower. Anther shape: Oblong. Anther size: About 1 mm by 5 mm. Anther color: 144A. Pollen amount: Moderate. Pollen color: 10A. Pistils: Quantity: One per flower. Pistil length: About 5.8 cm. Style length: About 5 cm. Style color: 145A. Stigma shape: Rounded. Stigma color: 144A. Ovary color: 144B. Seed/fruit: Seed and fruit development have not been observed on plants of the new *Anigozanthos*.

*Temperature tolerance.*—Plants of the new *Anigozanthos* have been observed to tolerate temperatures from about 0° C. to about 40° C.

Pathogen/pest resistance: Plants of the new *Anigozanthos* have not been observed to be resistant to pests and pathogens common to *Anigozanthos*.

It is claimed:

1. A new and distinct *Anigozanthos* plant named 'Rambudan' as illustrated and described.

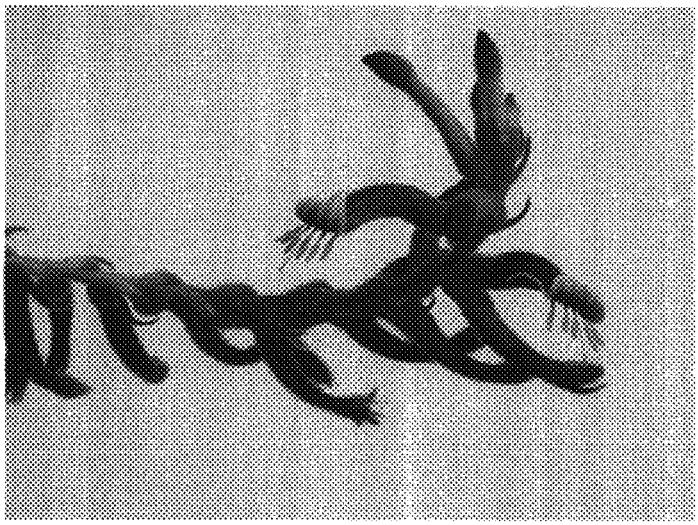
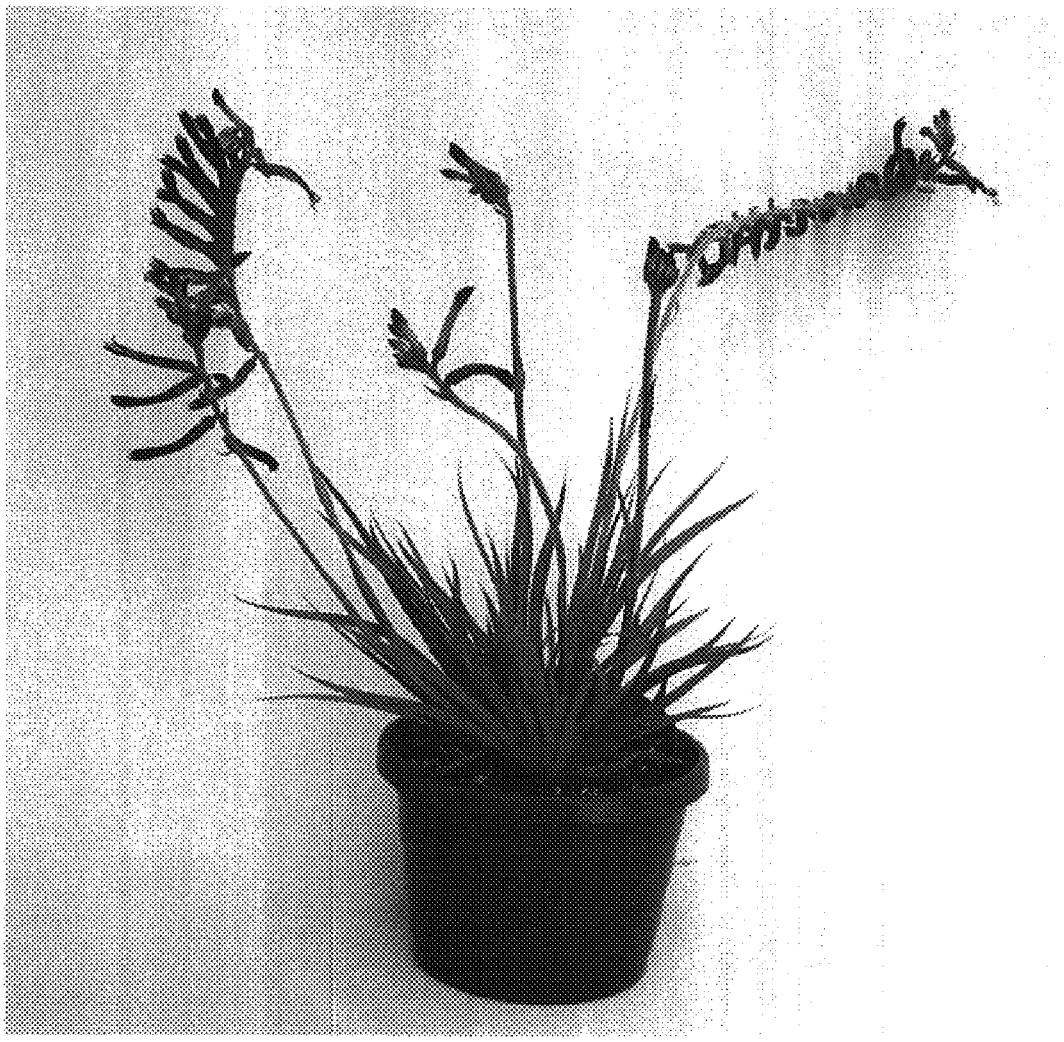

* * * * *